(12) United States Patent
Fard

(10) Patent No.: US 6,386,201 B1
(45) Date of Patent: May 14, 2002

(54) APPARATUS FOR PREVENTING SNORING

(76) Inventor: Bijan Golriz Fard, Hohe Linde 2, D-30519 Hannover (DE)

( * ) Notice: Subject to any disclaimer, the term of this patent is extended or adjusted under 35 U.S.C. 154(b) by 0 days.

(21) Appl. No.: 09/849,628

(22) Filed: May 4, 2001

(51) Int. Cl.[7] .................................................. A61F 5/56
(52) U.S. Cl. ........................ 128/848; 602/902; 5/655
(58) Field of Search ............................... 128/846, 845, 128/848; 5/655, 657; 602/902

(56) References Cited

U.S. PATENT DOCUMENTS

| | | | | |
|---|---|---|---|---|
| 4,780,921 A | * | 11/1988 | Lahn | 5/437 |
| 4,918,774 A | * | 4/1990 | Popitz | 5/441 |
| 4,941,478 A | * | 7/1990 | Takeuchi | 128/848 |
| 6,240,316 B1 | * | 5/2001 | Richmond | 602/42 |

FOREIGN PATENT DOCUMENTS

| | | |
|---|---|---|
| DE | 3727258 C2 | 12/1990 |
| DE | 9100663 U1 | 5/1991 |
| DE | 4137631 A1 | 5/1992 |
| DE | 19535232 C2 | 7/1998 |
| JP | 1085108 | 4/1998 |

* cited by examiner

*Primary Examiner*—Michael A. Brown
(74) *Attorney, Agent, or Firm*—Flanagan & Flanagan; John R. Flanagan

(57) ABSTRACT

An apparatus for preventing snoring includes a pillow divided internally into separate air chambers, a sound sensor, an air pressure source, an air pressure reducing unit, and a monitoring unit. The monitoring unit is activated by snoring noises sensed by the sound sensor, is operable to acquire the position of a sleeper's head on the pillow by sensing pressure increase in respective ones of the air chambers of the pillow resulting from the weight of the sleeper's head lying on the pillow, and, in response to such acquiring, is operable to control the operation of the air pressure source and the air pressure reducing unit so as to change the air pressure of selected ones of the air chambers of the pillow and thereby causes a change of the position of the sleeper's head which results in the sleeper stopping snoring.

16 Claims, 4 Drawing Sheets

APPARATUS FOR PREVENTING SNORING

BACKGROUND OF THE INVENTION

1. Field of the Invention

The present invention relates to devices for preventing snoring and, more particularly, is concerned with an apparatus for preventing snoring by acquiring and changing the position of a snoring sleeper's head on a pillow via sensing and changing the air pressure in separate air chambers in the pillow.

2. Description of the Prior Art

In German patent document No. DE 37 27 258 C2, a device is disclosed for preventing snoring. The device includes a housing which can be placed as a base underneath a pillow. The housing has a plurality of side walls and a cover rotatably connected with its side walls. An eccentric drive for the cover and an electric motor for driving the eccentric drive are disposed in the housing. Furthermore, an electronic system is disposed in the housing for converting snoring sounds, received via a microphone, into electric energy for operating the electric motor. The eccentric drive sets the housing cover into a rolling or tumbling motion, which is continued until the snoring ceases. A disadvantage of this device is that the housing, which by necessity is hard, together with the cover, which is also hard, significantly limits the sleeping comfort of the device.

In German patent document No. DE 41 37 631 A1, an apparatus is disclosed for raising a mattress at the margin thereof in an attempt to stop the snoring by a sleeper on the mattress. The apparatus includes an air-inflatable hollow body disposed on at least one of the two longitudinal margin regions of the mattress. The hollow body is normally empty and lies flat under the mattress. When a snoring sound from the sleeper on the mattress is received via a microphone, a motor driven pump unit is switched on. The pump unit rapidly fills and inflates the hollow body since the latter has a relatively small volume. The inflated hollow body lifts the at least one margin region of the mattress and thereby changes the position of the sleeper such that the snoring will ordinarily stop. If the snoring does not stop, the process must be repeated. A disadvantage of this apparatus is that through the movement of the entire body of the sleeper the sleep disturbance is persistent.

In German patent document No. DE 91 00 663 U1 a device is disclosed for reducing snoring. The device includes a roll-off structure which extends in the area of a pillow in extension of a longitudinal center line of the body of a sleeper. The roll-off structure is comprised of an inflatable hose. If the sleeper starts to snore, a noise sensor detects the snoring and switches on a pump which, in turn, inflates the hose. The inflating hose expands and presses against the back of the sleeper's head causing the sleeper to turn his or her head to the side. Instead of the noise sensor, the document discloses that a pressure sensor can be employed in the pillow. But, it is unclear how the pressure sensor is intended to work. Either the pressure sensor acts continuously since the sleeper's head is continuously in contact with it or the pressure sensor acts only when the sleeper's head moves into a different position and the pressure sensor is touched in the process. Both ways seem unworkable, however, since the sleeper in the former case would not be able to rest peacefully, and, in the second case, the pressure sensor would only trigger after what it intends to achieve, namely a head movement, would have already occurred.

In German patent document No. DE 195 35 232 CA, a device for stopping snoring is disclosed in the form of an adjustable support for a pillow. The adjustable support includes a movable bearing surface for the pillow. The bearing surface has a substantially rectangular configuration and thus has four sides. The adjustable support also includes a plurality of lifting elements disposed under the four sides of the bearing surface. The lifting elements are pneumatic pressure cushions which are connected to a common pump via valves actuatable by a control device. By actuating the pump, one of the lifting elements is filled with air and in this way the corresponding side of the bearing surface is raised. In such manner, a displacement of the sleeper's body into a side position is initiated or the sleeper's head is raised in the back or front. Potentially, after several position changes, the sleeper is placed in a sleeping position in which the snoring stops. The pump can be switched on via an acoustic sensor.

Lastly, in Japanese patent document No. 10-85108, an anti-snoring device is disclosed in the form of a pillow having several air chambers in it which are disposed one next to the other. These air chambers of the pillow are inflated to different degrees and are again vented whereby a movement of a sleeper's head is achieved.

All known anti-snoring devices operating with air chambers have in common the problem that the pressurization of the air chambers takes place randomly, that is, those of the air chambers which do not produce the desired effect are also pressurized. Consequently, a need exists for a device that will solve this problem with known anti-snoring device employing the pressurization of air chambers to prevent snoring.

SUMMARY OF THE INVENTION

The present invention provides an apparatus for preventing snoring which solves the aforementioned problem of the prior art devices in a manner that does not impair the sleeping comfort of the sleeper either at all or only insignificantly and yet effectively prevents snoring.

The snoring preventing apparatus of the present invention, which solves the aforementioned problem, comprises a pillow divided internally into a plurality of separate air chambers, a sound sensor for sensing snoring noises emanating from a sleeper's head resting on said pillow, means for sensing and changing air pressure being connected in flow communication individually with each of the separate air chambers of the pillow, and a monitoring unit connected to the sound sensor and to the air pressure sensing and changing means. The monitoring unit is activatable by snoring noises sensed by the sound sensor to operate so as to acquire the position of a sleeper's head on the pillow by operating the air pressure sensing and changing means so as to sense an increase of pressure in respective ones of the air chambers of the pillow resulting from the weight of the sleeper's head lying on the pillow. The monitoring unit also is operable in response to acquiring the position of the sleeper's head on the pillow to control the operation of the air pressure sensing and changing means so as to change the air pressure in selected ones of the air chambers of the pillow and thereby causes a change of the position of the sleeper's head resulting in the sleeper stopping snoring. The air pressure sensing and changing means preferably is at least one air pressure source and an air pressure reducing unit.

The pillow has a pair of lateral chambers each extending between a front and a rear of the pillow and along one of a pair of opposite sides of the pillow. The pillow also has front and back middle chambers extending between and transversely to the lateral chambers and disposed adjacent to one another and adjacent to the front and rear of the pillow. The pillow further has a cover layer overlying the chambers at a top of the pillow. The cover layer has a volume filled with a gel.

These and other features and advantages of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the following detailed description, reference will be made to the attached drawings in which.

DETAILED DESCRIPTION OF THE INVENTION

Figure 1:
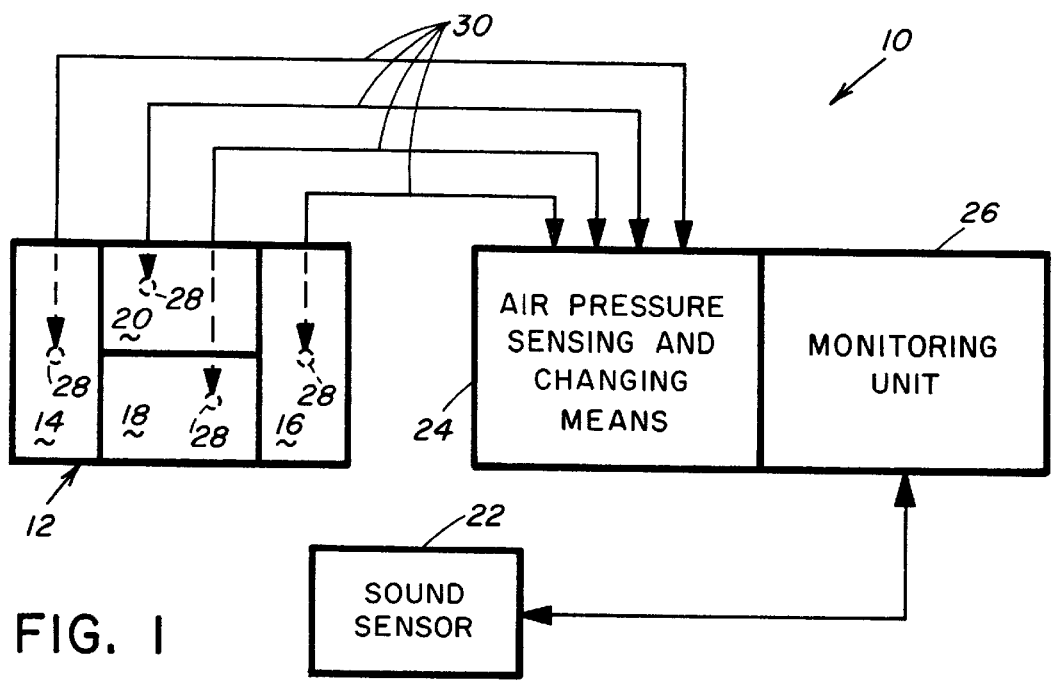
FIG. 1 is a general schematic block diagram of an apparatus of the present invention for preventing snoring.
Figure 3:
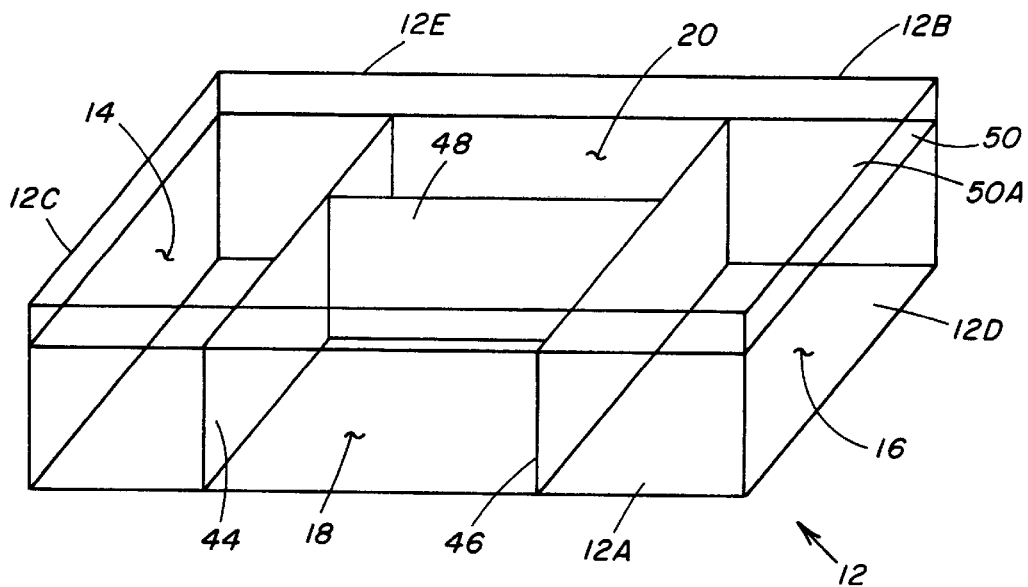
FIG. 3 is a perspective diagrammatic representation of a pillow of the snore preventing apparatus in a normal sleep position and as seen obliquely from the front and the top of the pillow.

Referring to the drawings and particularly to FIG. 1, there is illustrated a general schematic block diagram of an apparatus for preventing snoring, generally designated 10, in accordance with the present invention. The apparatus 10 basically includes a pillow 12 divided internally into a plurality of separate air chambers 14, 16, 18, 20, a sound sensor 22 for sensing snoring noises emanating from a sleeper's head resting on the pillow 12, means 24 for sensing and changing air pressure being connected in flow communication individually with each of the separate air chambers 14, 16, 18, 20 of the pillow 12, and a monitoring unit 26 connected to the sound sensor 22 and to the air pressure sensing and changing means 24. The monitoring unit 26 is activatable by snoring noises sensed by the sound sensor 22 to operate so as to acquire the position of a sleeper's head on the pillow 12 by operating the air pressure sensing and changing means 24 so as to sense an increase of pressure in respective ones of the air chambers 14, 16, 18, 20 of the pillow 12 resulting from the weight of the sleeper's head lying on the pillow 12. The monitoring unit 26 also is operable in response to acquiring the position of the sleeper's head on the pillow 12 to control the operation of the air pressure sensing and changing means 24 so as to change the air pressure in selected ones of the air chambers 14, 16, 18, 20 of the pillow 12 and thereby causes a change of the position of the sleeper's head resulting in the sleeper stopping snoring.

Figure 2:
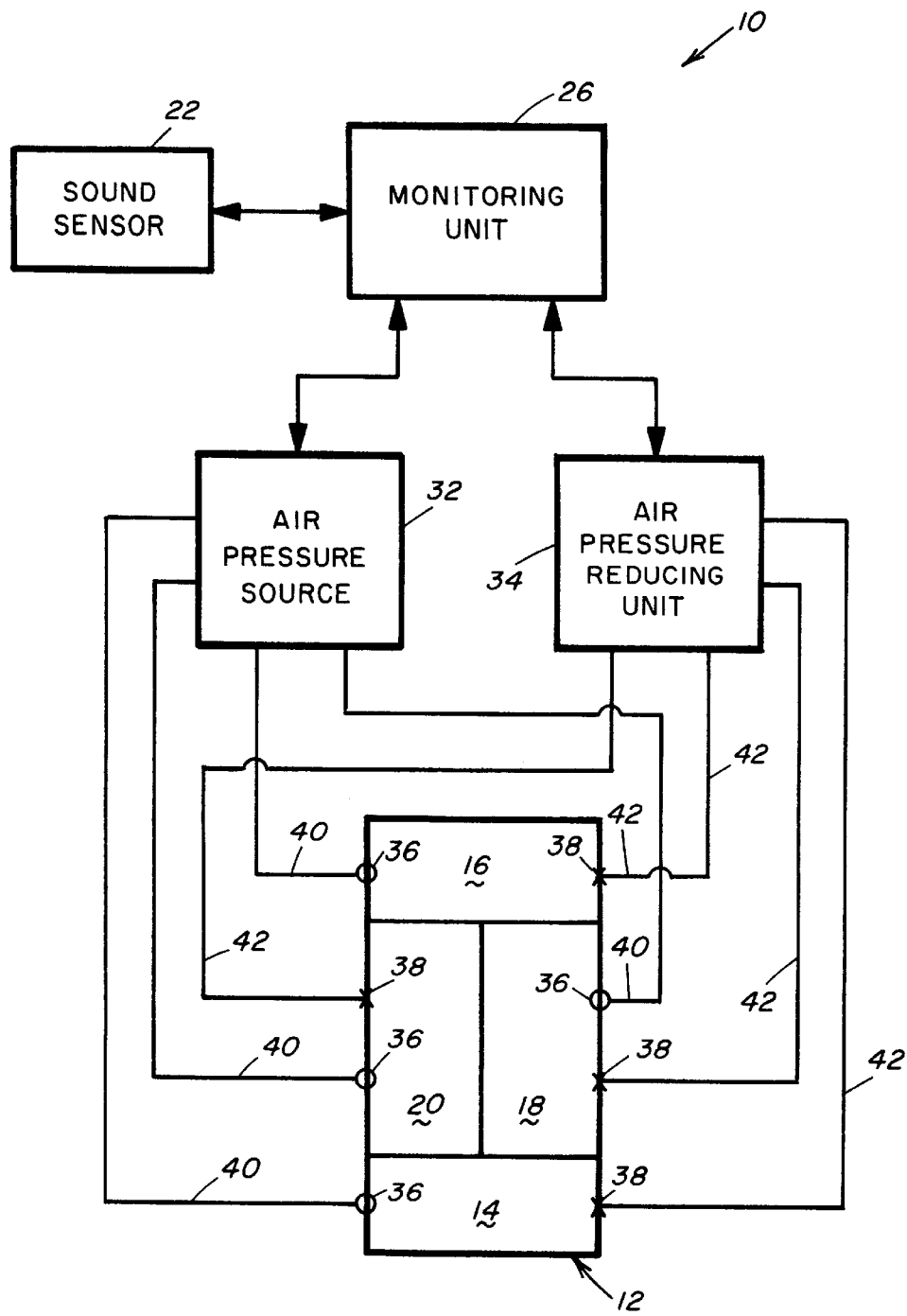
FIG. 2 is a more detailed schematic block diagram of the apparatus of the present invention.
Figure 4:
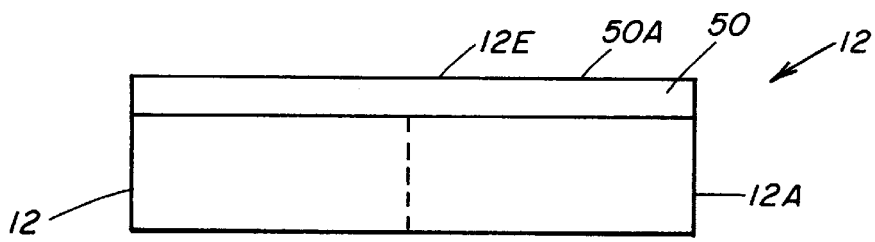
FIG. 4 is a side elevational diagrammatic representation of the pillow as seen along line 4—4 of FIG. 3.
Figure 5:
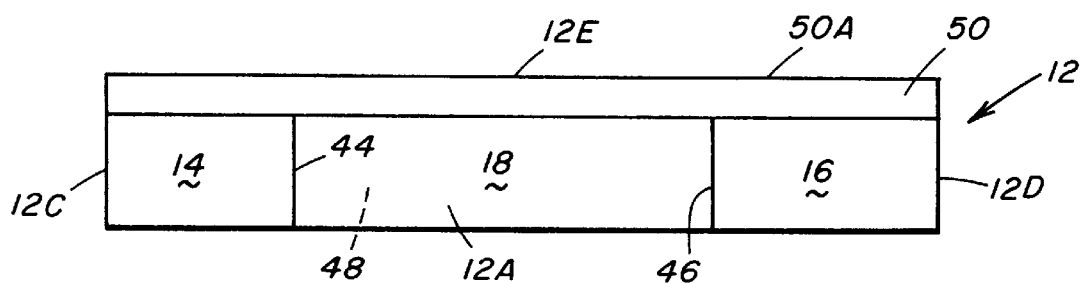
FIG. 5 is a front elevational diagrammatic representation of the pillow as seen along line 5—5 of FIG. 3.
Figure 6:
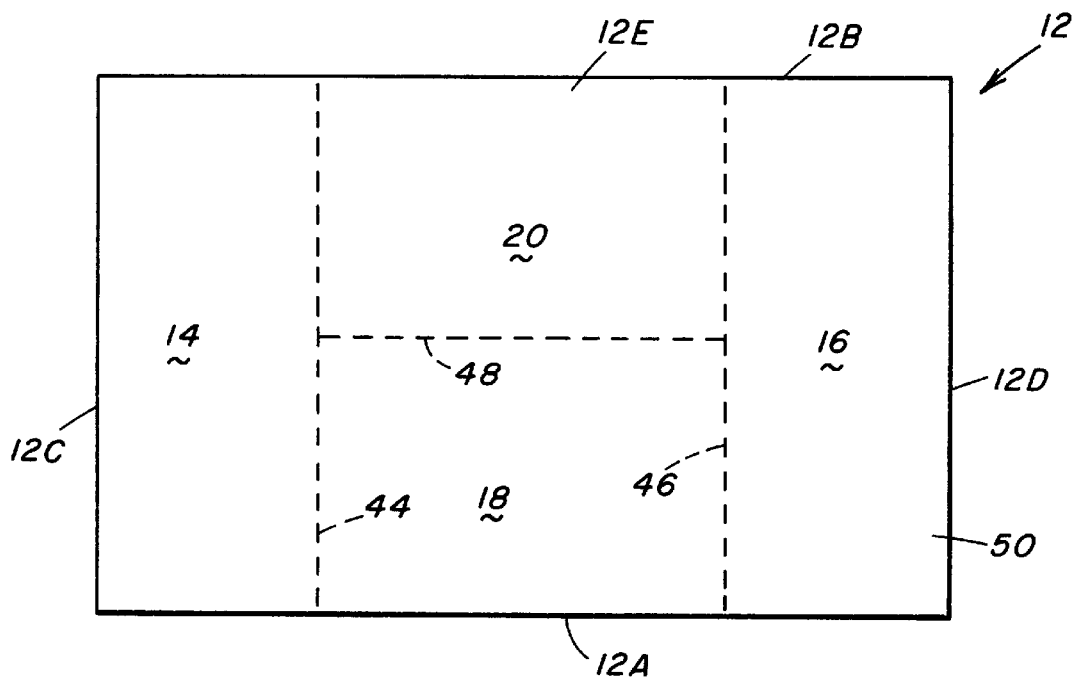
FIG. 6 is a top plan diagrammatic representation of the pillow of FIG. 5.

Each of the chambers 14, 16, 18, 20 includes a port 28 which is connected in air communication via a line 30 to the air pressure sensing and changing means 24. More particularly, as seen in the more detailed schematic block diagram of FIG. 2, the air pressure sensing and changing means 24 preferably takes the form of an air pressure source 32, which can be an air pressure compressor, and an air pressure reducing unit 34, which can be an air pressure venting valve. The air pressure source 32 and the air pressure reducing unit 34 are connected in flow communication individually with each of the separate air chambers 14, 16, 18, 20 of the pillow 12 at separate inlets and outlets 36, 38 of the ports 28 thereof by pairs of inflow and outflow lines 40, 42. The sound sensor 22, which can be a microphone, is disposed in the proximity of the pillow 12 and the sleeper's head. When snoring noises occur, corresponding signals of the sound sensor 22 activate the monitoring unit 26 such that the monitoring unit 26 via the operation of the air pressure source 32 and air pressure reducing unit 34 acquires the local position of the sleeper's head with respect to the air chambers 14, 16, 18, 20. The monitoring unit 26 which is comprises of a suitable arrangement of logic circuitry, pressure sensors and air conduits and valves, in turn, controls the operation of the air pressure source 32 by switching it on or off and, if appropriate, controls the operation of the air pressure reducing unit 34 by opening or closing it such that the air pressure in the appropriate ones of the air chambers 14, 16, 18, 20 is changed so as to effect the desired movement of the sleeper's head and thus change of the position of the head on the pillow 12 so that the snoring will stop.

Referring to FIGS. 3–6, there is illustrated an exemplary embodiment of the plurality of separate air chambers 14, 16, 18, 20 of the pillow 12. These air chambers include a pair of lateral chambers 14, 16 each extending between a front 12A and a rear 12B of the pillow 12 and along one of a pair of opposite (left and right) sides 12C, 12D of the pillow 12. These air chambers also include front and back middle chambers 18, 20 extending between and transversely to the lateral chambers 14, 16 and disposed adjacent to one another and adjacent to the front 12A and rear 12B of the pillow 12. The air chambers 14, 16, 18, 20 are defined by and separated airtight from one another by flexible partition walls 44, 46, 48. The partition walls 44, 46 extend between and attach to the front 12A and back 12B of the pillow 12, whereas the partition wall 48 extends between and attaches to the partition walls 44, 46 at locations thereon substantially equidistant between their opposite ends.

The pillow 12 further has a cover layer 50 overlying the air chambers 14, 16, 18, 20 at a top 12E of the pillow 12 such that the air chambers 14, 16, 18, 20 occupy the entire space of the pillow 12 located below the cover layer 50. The cover layer 50 preferably is of a soft consistency and can be comprised, for example, of a foamed material. It is particularly advantageous if the cover layer 50 comprises a volume filled with a gel, since the cover layer 50 serves for localizing the sleeper's head as well as for conveying a very pleasant sensation with the head resting on it. In order to ensure good ventilation of the head region, the surface 50A of the cover layer 50 can be perforated. Onto the surface 50A can also additionally be laminated a thin layer of a foamed material.

Figure 7:
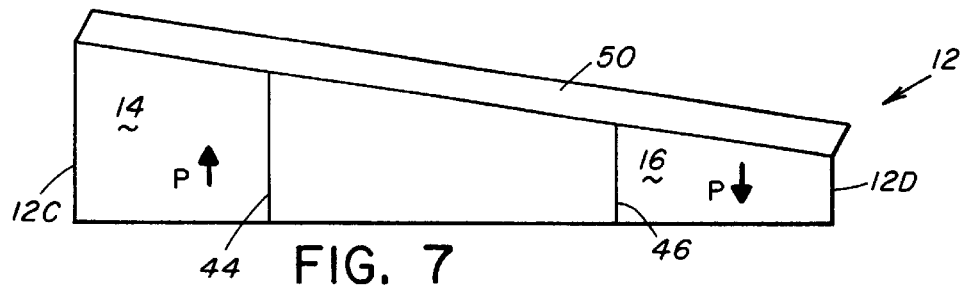
FIG. 7 is an enlarged front elevational diagrammatic representation of the pillow similar to FIG. 5, but now with the 20 pillow shown activated such that a top cover layer thereof slopes downward from the left to the right of the pillow.
Figure 8:
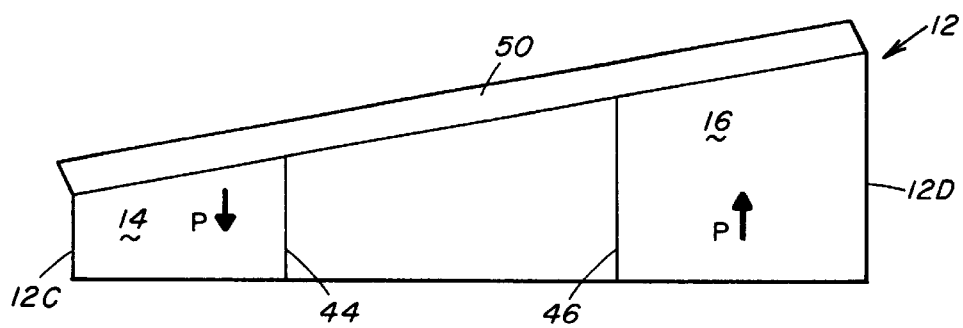
FIG. 8 is an enlarged front elevational diagrammatic representation of the pillow similar to FIG. 5, but now with the pillow shown activated such that the top cover layer thereof slopes downward from the right to the left of the pillow.
Figure 10:
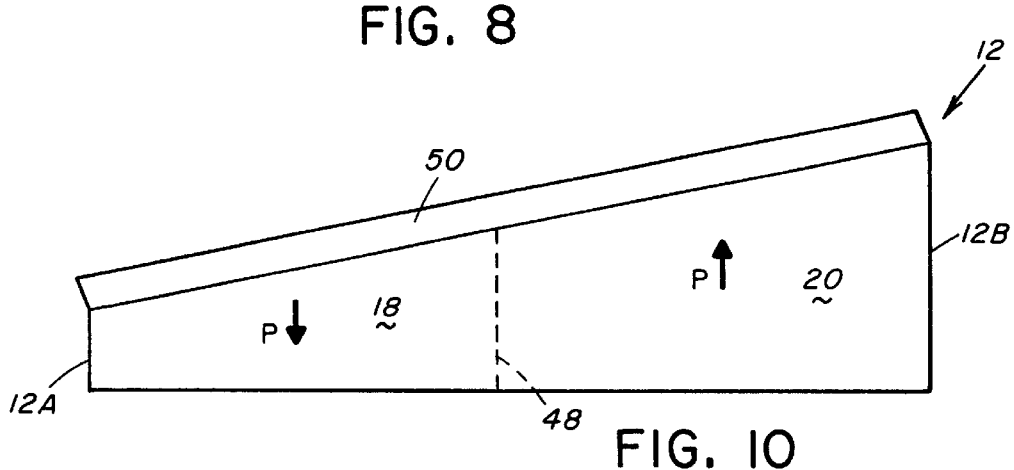
FIG. 10 is an enlarged side elevational diagrammatic representation of the pillow similar to FIG. 4, but now with the pillow shown activated such that the top cover layer thereof slopes downward from the rear to the front of the pillow.
Figure 9:
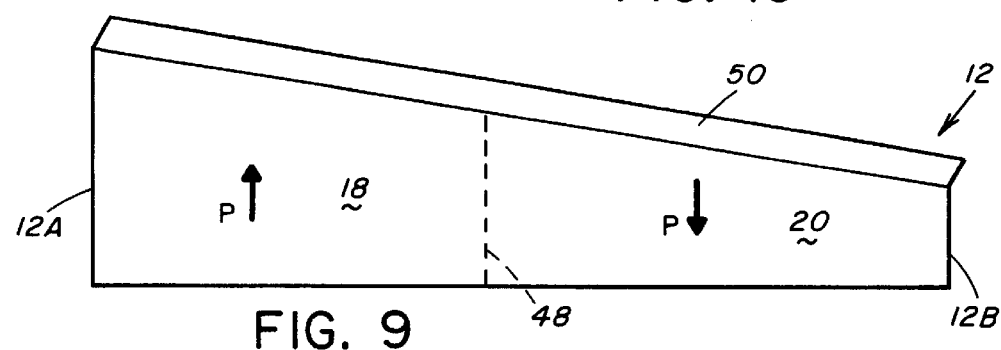
FIG. 9 is an enlarged side elevational diagrammatic representation of the pillow similar to FIG. 4, but now with the pillow shown activated such that the top cover layer thereof slopes downward from the front to the rear of the pillow.

The division of the pillow 12 into the pattern of the air chambers 14, 16, 18, 20 as provided in the exemplary embodiment shown in FIGS. 3–6 ensures movement of the sleeper's head in all directions by changing the air pressure in the air chambers as shown FIGS. 7–10. In FIG. 7, the lateral chambers 14, 16 of the pillow 12 are shown activated such that the top cover layer 50 slopes downward from the left side 12C to the right side 12D of the pillow 12. The air pressure in the left lateral chamber 14 is increased while the air pressure in the right lateral chamber 16 is decreased to cause such sloping of the cover layer So which results in a rotation toward the right side 12D of the pillow 12 of the sleeper's head that was initially facing toward the left side 12C of the pillow 12. In FIG. 8, the lateral chambers 14, 16 of the pillow 12 are shown activated such that the top cover layer 50 slopes downward from the right side 12D to the left side 12C of the pillow 12. The pressurization of the lateral chambers 14, 16 is now the reverse of that shown in FIG. 7 to cause such reverse sloping of the cover layer 50 which results in a rotation toward the left side 12C of the pillow 12 of the sleeper's head that was initially facing toward the right side 12D of the pillow 12. In FIG. 9, the front and rear middle chambers 18, 20 of the pillow 12 are shown activated such that the top cover layer 50 slopes downward from the front 12A to the rear 12B of the pillow 12. An increase in the air pressure in the front middle chamber 18 and a reduction in the air pressure in the rear middle chamber 20 causes such sloping of the cover layer 50 which results in a retroversion of the head, that is, a rearward movement or extension of the head. In FIG. 10, the front and rear chambers 18, 20 of the pillow 12 are shown activated such that the top cover layer 50 slopes downward from the front 12A to the rear 12B of the pillow 12. The pressurization of the front and rear middle chambers 18, 20 is now the reverse of that shown in FIG. 9 to cause such reverse sloping of the cover layer 50 which results in an anteversion of the head, that is, the head becomes tilted forward. It is to be understood that the above-described movements can also be combined. The greater the number of chambers, the greater the options for changing the form of the pillow surface.

In conclusion, apparatus 10 of the present invention utilizes the fact that depending on the position of a sleeper's head the weight of a sleeper's head on the pillow 12 exerts pressure differently onto particular ones of the chambers 14, 16, 18, 20 of the pillow 12 and such differences in the pressure exerted is used by the monitoring unit 26 to acquire the local position of the head on the pillow 12. The pressure increase resulting therefrom in one chamber or several chambers 14, 16, 18, 20 is acquired by the monitoring unit 26 which permits the selecting and transferring specifically to those of the chambers 14, 16, 18, 20 a compressed air charging or reducing that yields the desired effect, that is, the head movement and thereby the desired change in the position of the sleeper's head on the pillow 12. Pressurization is thus avoided in those of the chambers 14, 16, 18, 20 which would be ineffective due to their position with respect to the sleeper's head. The monitoring unit 26 can also be utilized for the purpose of statistically acquiring the local position the sleeper's head in which snoring is generated with especially high frequency.

It is thought that the present invention and its advantages will be understood from the foregoing description and it will be apparent that various changes may be made thereto without departing from the spirit and scope of the invention or sacrificing all of its material advantages, the form hereinbefore described being merely preferred or exemplary embodiment thereof.

I claim:

1. An apparatus for preventing snoring, comprising:
   (a) a pillow divided internally into a plurality of separate air chambers;
   (b) a sound sensor for sensing snoring noises emanating from a sleeper's head resting on said pillow;
   (c) mean for sensing and changing air pressure being connected in flow communication individually with each of said separate air chambers of said pillow; and
   (d) a monitoring unit connected to said sound sensor and to said air pressure sensing and changing means such that said monitoring unit is activatable by snoring noises sensed by said sound sensor to operate so as to acquire the position of a sleeper's head on said pillow by operating said air pressure sensing and changing means so as to sense an increase of pressure in respective ones of said air chambers of said pillow resulting from the weight of the sleeper's head lying on said pillow, said monitoring unit also being operable in response to acquiring the position of the sleeper's head on said pillow to control the operation of said air pressure sensing and changing means so as to change the air pressure in selected ones of said air chambers of said pillow and thereby causes a change of the position of the sleeper's head resulting in the sleeper stopping snoring.

2. The apparatus of claim 1 wherein said air pressure sensing and changing means includes at least one air pressure source.

3. The apparatus of claim 1 wherein said air pressure sensing and changing means includes an air pressure reducing unit.

4. The apparatus of claim 1 wherein said pillow has a cover layer overlying said chambers at a top of said pillow.

5. The apparatus of claim 4 wherein said cover layer has a volume filled with a gel.

6. The apparatus of claim 1 wherein said pillow has a pair of lateral chambers each extending between a front and a rear of said pillow and along one of a pair of opposite sides of said pillow.

7. The apparatus of claim 6 wherein said pillow also has front and back middle chambers extending between and transversely to said lateral chambers and disposed adjacent to one another and adjacent to said front and rear of said pillow.

8. The apparatus of claim 7 wherein said pillow further has a cover layer overlying said chambers at a top of said pillow.

9. The apparatus of claim 8 wherein said cover layer has a volume filled with a gel.

10. An apparatus for preventing snoring, comprising:
   (a) a pillow divided internally into a plurality of separate air chambers;
   (b) a sound sensor for sensing snoring noises emanating from a sleeper's head resting on said pillow;
   (c) at least one air pressure source connected in flow communication individually with each of said separate air chambers of said pillow;
   (d) an air pressure reducing unit connected in flow communication individually with each of said separate air chambers of said pillow; and (e) a monitoring unit connected to said sound sensor, said air pressure source and said air pressure reducing unit such that said monitoring unit is activatable by snoring noises sensed by said sound sensor to operate so as to acquire the position of a sleeper's head on said pillow by operating said air pressure source and air pressure reducing unit so as to sense an increase of pressure in respective ones of said air chambers of said pillow resulting from the weight of the sleeper's head lying on the pillow, said monitoring unit also being operable in response to acquiring the position of the sleeper's head on said pillow to control operation of said air pressure source and air pressure reducing unit so as to change the air pressure of selected ones of said air chambers of said pillow and thereby causes a change of the position of the sleeper's head resulting in the sleeper stopping snoring.

11. The apparatus of claim 10 wherein said pillow has a cover layer overlying said chambers at a top of said pillow.

12. The apparatus of claim 11 wherein said cover layer has a volume filled with a gel.

13. The apparatus of claim 10 wherein said pillow has a pair of lateral chambers each extending between a front and a rear of said pillow and along one of a pair of opposite sides of said pillow.

14. The apparatus of claim 13 wherein said pillow also has front and back middle chambers extending between and transversely to said lateral chambers and disposed adjacent to one another and adjacent to said front and rear of said pillow.

15. The apparatus of claim 14 wherein said pillow further has a cover layer overlying said chambers at a top of said pillow.

16. The apparatus of claim 15 wherein said cover layer has a volume filled with a gel.

* * * * *